United States Patent
Moy et al.

(10) Patent No.: US 8,119,711 B2
(45) Date of Patent: Feb. 21, 2012

(54) OLIGOMERIC BISPHOSPHATE FLAME RETARDANTS AND COMPOSITIONS CONTAINING THE SAME

(75) Inventors: Paul Y. Moy, Fishkill, NY (US); Andrew Gregor, II, Hopewell Junction, NY (US); Ronald L. Pirelli, Mahopac, NY (US); Danielle A. Bright, New City, NY (US); Leslie Bright, legal representative, New City, NY (US)

(73) Assignee: ICL-IP America Inc., Ardsley, NY (US)

( * ) Notice: Subject to any disclaimer, the term of this patent is extended or adjusted under 35 U.S.C. 154(b) by 221 days.

(21) Appl. No.: 12/310,454

(22) PCT Filed: Aug. 30, 2007

(86) PCT No.: PCT/US2007/019172
§ 371 (c)(1),
(2), (4) Date: Nov. 23, 2009

(87) PCT Pub. No.: WO2008/027536
PCT Pub. Date: Mar. 6, 2008

(65) Prior Publication Data
US 2011/0034597 A1     Feb. 10, 2011

(51) Int. Cl.
*C08K 5/51* (2006.01)
(52) U.S. Cl. ............................. 524/147; 524/127; 558/70
(58) Field of Classification Search ............... 524/127, 524/147; 558/70
See application file for complete search history.

(56) References Cited

U.S. PATENT DOCUMENTS 5,420,327 A     5/1995     Bright et al.

FOREIGN PATENT DOCUMENTS

| DE | 2411029 | | 9/1974 |
|---|---|---|---|
| EP | 0 338 434 A2 | * | 10/1989 |
| EP | 338434 | | 10/1989 |
| EP | 0 672 717 A1 | * | 9/1995 |
| EP | 0672717 | | 9/1995 |
| FR | 2 763 952 | * | 6/1997 |
| FR | 2763952 | | 12/1998 |
| GB | 1 405 983 | * | 9/1975 |
| GB | 1405983 | | 9/1975 |
| JP | 49-002850 | | 1/1974 |
| JP | 7-109406 | | 4/1995 |
| JP | 9-132720 | | 5/1997 |
| JP | 09-132720 | * | 5/1997 |

OTHER PUBLICATIONS

Wang et al. J. of Shandong Institute of Building Materials, p. 25-27 (1998).*
Wang, Xiaomei et al.: "Synthesis of Condensed Phosphates as Flame Retardant for Polymers," Shandong Jiancai Xueyuan Xuebo, 12(1), pp. 25-27, 1998.
Wang, Xiaomei et al.: "Synthesis of Brominated Polyphenyl Phosphate Powder as Fireproofing Agent for Decorative Boards," Huagong Jinzhan, 17(4), pp. 54-55 & 61, 1998.
Beilstein Institute for Organic Chemistry, 1975 "Phosphoric Acid 4-[(Bis(3,5-Dimethyl-Phenoxyl-Phosphoryloxy]-Phenyl Ester Bis(3,5-Dimethyl-Phenyl) Ester," IOVU, Viona: Rev. Chim, vol. 26, 1975, p. 805.

* cited by examiner

*Primary Examiner* — Ling-Siu Choi
(74) *Attorney, Agent, or Firm* — Dilworth & Barrese, LLP

(57) ABSTRACT

An oligomeric phosphate or mixture of oligomeric phosphates having the general formula (I) wherein $R_1$, $R_2$, $R_3$ and $R_4$ each independently is aryl or alkaryl and n has an average value of from about 1.0 to about 2.0 and resin compositions containing the same.

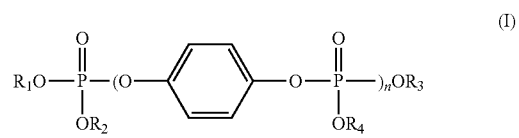

(I)

12 Claims, No Drawings

OLIGOMERIC BISPHOSPHATE FLAME RETARDANTS AND COMPOSITIONS CONTAINING THE SAME

FIELD OF THE INVENTION

The present invention relates to oligomeric bis-phosphate flame retardants and more particularly to oligomeric hydroquinone bis-phosphate flame retardants and resin compositions containing the same.

BACKGROUND OF THE INVENTION

Oligomeric bis-phosphates, which are useful as flame retardants in resin compositions such as polycarbonate (PC)/styrenic containing alloys, are typically in the form of viscous liquids and require special equipment for handling during processing, especially in cold climate locations. The viscous liquid phosphates are often pumped into compounding extruders after the thermoplastic polymers, i.e. resins, are melted through heat and mechanical shear. Specialized equipment may include heated reservoirs with heat-traced supply lines designed to keep the oligomeric bis-phosphates fluid so as not to interfere with the extrusion process. Even with the use of specialized equipment, additional steps need to be taken during processing so as to avoid this problem and other problems.

Alternatively, solid phosphate ester flame retardants such as triphenyl phosphate, which is typically available in a flaked form, can be used. However, these solid phosphate ester flame retardants tend to melt prematurely in the feed zone of the extruder causing the composite pre-mixture to "bridge" thereby interfering with the mixing operation.

In view of the foregoing, what is needed are flame retardants for use in resin compositions that have improved physical characteristics and avoid the processing problems described above. Accordingly, the invention herein is directed to oligomeric bis-phosphate flame retardants having desirable physical properties and characteristics which when compounded with resins provide compositions having excellent flame retardancy and improved physical properties, as Compared with previously provided flame retarded resin compositions.

SUMMARY OF THE INVENTION

The present invention is directed to flame-retardant oligomeric phosphates or blends of oligomeric phosphates having the general formula I:

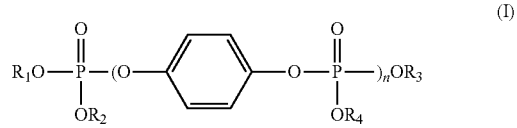

wherein $R_1$, $R_2$, $R_3$ and $R_4$ each independently is aryl or alkaryl and n has an average value of from about 1.0 to about 2.0 and resin compositions containing the same.

In one aspect of the present invention, it has been surprisingly found that oligomeric phosphates within general formula I, wherein n has an average value of about 1.0 to about 1.1, are in the form of free-flowing powders. Typically, but not limited thereto, "free-flowing powder" as applied to the oligomeric phosphates of formula I have average particle sizes of about 10 μm to about 80 μm. These free-flowing powders, when compounded with resins, avoid the previously discussed handling problems as well as impart improved physical properties such as, UV stability, greater hydrolytic stability and higher heat distortion temperature (HDT) to the resin compositions as compared with previously provided oligomeric phosphate containing flame-retarded resin compositions.

In another aspect of the invention, oligomeric phosphates within the general formula I, wherein n has an average value greater than about 1.1, while characterized as waxy-like solids, still unexpectedly impart improved UV stability, hydrolytic stability and higher HDT values to resin compositions containing the same as compared with resin compositions containing previously employed oligomeric phosphate flame retardants.

DETAILED DESCRIPTION OF THE INVENTION

The present invention is directed to oligomeric phosphate flame retardants and resin compositions containing the same. In particular, the present invention is directed to oligomeric hydroquinone bis-phosphate flame retardants having the structure of formula (I) above wherein preferably $R_1$, $R_2$, $R_3$ and $R_4$ each independently is a phenyl group of general formula II:

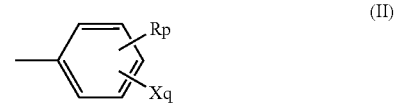

wherein each R independently is alkyl of 1 to 4 carbon atoms, each X independently is chlorine or bromine, p is 0 to 3 and q is 0 to 5 with the sum of p and q being 0 to 5 and n has an average value of from about 1.0 to about 2.0, preferably from about 1.0 to less than or equal to about 1.2, and more preferably from about 1.0 to about 1.1. A particularly preferred oligomeric bis-phosphate within formula I above is hydroquinone bis-(diphenylphosphate), i.e., $R_1$, $R_2$, $R_3$ and $R_4$ are each phenyl.

In the general, the oligomeric hydroquinone bis-phosphates of the present invention are prepared by reacting a diaryl halophosphate with hydroquinone in the presence of a catalyst. In a preferred embodiment of the invention, diphenylchlorophosphate (DPCP) is reacted with hydroquinone in the presence of $MgCl_2$ to produce hydroquinone bis-(diphenylphosphate). In accordance with the present invention, hydroquinone bis(diphenylphosphate) within general formula I prepared by this process will have an average n value of about 1.1 or less, such as prepared in Example 1 below.

In another embodiment, the hydroquinone bis-phosphate oligomers of the present invention are prepared by reacting hydroquinone with a reaction mixture comprising a diarylhalophosphate (such as diphenylchlorophosphate) and a monoaryldthalophosphate (such as monophenyl dichlorophosphate (MPCP)) in the presence of a catalyst, such as $MgCl_2$. A process such as this is described in U.S. Pat. No. 5,457,221, the entire contents of which are incorporated by reference herein. In accordance with the present invention, hydroquinone bis-phosphate oligomers within general formula I prepared by this process will have an average n value of from about 1.1 to about 2.0 and are generally waxy-like solids, such as prepared in Example 2 below.

In one preferred embodiment of the invention, high purity (99%) diphenyl-chlorophosphate (DPCP) is reacted with hydroquinone to yield essentially pure dimer, i.e. average n value of about 1.02, as illustrated by Example 1 below. The relatively pure dimer has a higher melting point than oligomers prepared from less pure DPCP and provides for a free-flowing powder product.

Typically, the value of n in formula I is calculated by firstly determining the proportions of oligomeric phosphate species (oligophosphates) in the product by high pressure liquid chromatography (HPLC) measurements. The weight average (n) value is then determined (calculated) in known manner from the proportions of the oligophosphates. In calculating the value of n, monophosphate species, e.g. triphenylphosphate, may or may not be included in the calculation. The n values ascribed to the oligomeric bis-phosphates of the present invention were calculated omitting the monophosphate species in the calculation. However, if the monophosphate species are considered (used) in the calculation, lower n values, depending on the amount of monophosphate species present, may result.

The present invention is also directed to resin compositions comprising a flame retardant effective amount of the oligomeric flame retardants of formula I and at least one resin. The resins used in the compositions of the present invention include but are not limited to styrenic polymers and copolymers, polyphenylene oxide (PPO), acrylonitrile butadiene styrene (ABS), polycarbonate (PC) and mixtures thereof. Specific resins used include PC/ABS mixtures, high impact polystyrene (HIPS) and PPO/HIPS. These types of resins or polymer mixtures are described for example in U.S. Pat. No. Re. 36,188, U.S. Pat. Nos. 6,727,301 and 6,753,366 the entire contents of which are incorporated by reference herein. The flame-retarded resin compositions of the present invention are typically useful, for example, in the production of domestic appliances, castings for electrical devices, bedding, furniture and automotive components.

The amount of oligomeric phosphate flame retardant typically used in the resin compositions of the present invention generally range from about 2% to about 20%, by weight, of the total weight of the composition, preferably from about 7% to about 15%, by weight, of the total weight of the composition, with the remainder being resin. The flame retarded resin compositions of the present invention can also include other additives such as antioxidants, stabilizers, fillers as well as other flame retardants.

A preferred flame retarded resin composition of the present invention comprises an effective flame retardant amount of hydroquinone bis-(diphenylphosphate) having an average value of n of about 1.02, a polycarbonate and a styrene-containing resin copolymer. A representative polycarbonate that can be used in the compositions of the present invention is Lexan, commercially available from General Electric Company.

The following examples are used to illustrate the present invention.

EXAMPLES

Example 1

The following table identifies the reaction mixture used in the preparation of a flame-retardant oligomeric hydroquinone bis(diphenylphosphate) in accordance with the present invention.

| Reaction Mixture | wt. (g) | moles |
|---|---|---|
| diphenyl chlorophosphate | 1087.8 | 4.0492 |
| Hydroquinone | 295.1 | 2.0246 |
| magnesium chloride ($MgCl_2$) (catalyst) | 3.2414 | 0.0340 |

Equipment:
A reaction calorimeter with a glass reactor, chiller for the condenser, and caustic scrubber system.

Procedure:
Diphenyl chlorophosphate, hydroquinone and $MgCl_2$ were charged to the reactor under an atmosphere of $N_2$. TR (temperature of reaction) was raised slowly to 140° C. over a 1 hour period.

At approximately 104° C., hydroquinone was almost completely dissolved, HCl gas evolution began and was visible.

As the reaction temperature approached the set point temperature (140° C.), the HCl gas evolution was very rapid. The temperature was held at 140° C. for about 10 hours. The reaction was completed and cooled to room temperature after reaching the endpoint acid number titration value of one or less.

The temperature of the crude reaction mixture was raised slowly to about 107° C. over a 30 minute period and was toluene added to the crude reaction mixture to facilitate washing of the material. The washing of the crude reaction mixture was performed at 85-90° C. with approximately 1000 grams of a 0.4% aqueous oxalic acid solution followed by deionized water then followed by 1000 grams of a 3.5% aqueous sodium hydroxide and finished by deionized water. The pH of the final wash was about 7.

Toluene/water mixture was removed from the washed product via a rotary evaporator under vacuum and at temperatures of about 95° to about 99° C. and then dried in an oven at 110° C. overnight to become totally molten. The next day the molten product was poured into a stainless steel pan to facilitate crystallization.

An 82% yield of a fine white free-flowing powdery product was recovered and identified as hydroquinone bis(diphenylphosphate), having an average n value of about 1.02.

The product was analyzed, using High Pressure Liquid Chromatography (HPLC), for phenol, toluene, triphenylphosphate (TPP) and oligomeric content and the results are reported as normalized area percent (Norm A %) and weight percent (wt %) in the table below. $P_2$ to $P_6$ refers to the number of phosphorus atoms in the oligomer.

| HPLC DATA | | |
|---|---|---|
| | Norm A % | Wt % |
| Phenol | 0.00 | <0.01 |
| Toluene | 0.29 | 0.34 |
| TPP | 0.56 | 0.60 |
| P2 | 97.58 | 97.90 |
| P3 | 1.27 | |
| P4 | 0.24 | |
| P5 | 0.04 | |
| P6 | 0.01 | |

As can be seen from the data above, the final product is almost 98% pure dimer of hydroquinone bis(diphenylphosphate). The product obtained is a free-flowing powder having an average n value of about 1.02, as determined in known manner from the proportions of individual constituent oligophosphates obtained by HPLC.

Example 2

The same procedure as described in Example 1 was used for preparation of oligomeric hydroquinone bis(diphenylphosphate) (HDP) of the present invention wherein the process utilizes the addition of monophenyl dichlorophosphate (MPCP) to produce an oligomeric product (HDP) having an average n value of about 1.15, as determined in known manner using the proportions of the individual constituent oligophosphates obtained by HPLC.

| Reaction Mixture* | wt. (g) | moles |
|---|---|---|
| diphenyl chlorophosphate | 977.60 | 3.638 |
| monophenyl dichlorophosphate | 49.76 | 0.236 |
| Triphenylphosphate* | 31.34 | 0.096 |
| Hydroquinone | 225.40 | 2.047 |
| magnesium chloride (MgCl$_2$) | 1.6246 | 0.017 |

*The reaction mixture contained a small amount of unreactive triphenylphosphate which is present as a by-product in the production of the diphenyl chlorophosphate and monophenyl dichlorophosphate as described in U.S. Pat. No. 5,457,221.

An 87% yield of the product was recovered. The white solid recovered appeared to have a waxy-like texture and was not free-flowing. The waxy-like texture of the recovered material presumably was due to the presence of other oligomeric phosphorus species in addition to the dimer.

The product was analyzed using HPLC and the results presented in the table below. Here, in contrast to Example 1, higher amounts of other oligomeric phosphate species are present. The hydroquinone bis(diphenylphosphate) oligomer blend obtained was a waxy-like solid having average n value of about 1.15 as determined in known manner using the proportions of the individual oligophosphates obtained by HPLC.

| HPLC DATA | | |
|---|---|---|
| | Norm A % | Wt % |
| Phenol | 0.01 | 0.01 |
| Toluene | 0.00 | 0 |
| TPP | 3.45 | 3.68 |
| P2 | 79.41 | 79.20 |
| P3 | 13.93 | |
| P4 | 2.61 | |
| P5 | 0.49 | |
| P6 | 0.10 | |

PC/ABS resin compositions containing the hydroquinone-bis(diphenylphosphate) (HDP) (average n value of 1.02) free-flowing powder obtained in Example 1 were compared with PC/ABS resins containing resorcinol bis(diphenylphosphate) (Fyrolflex RDP) (average n value of 1.28), bisphenol A bis(diphenylphosphate) (Fyrolflex BDP) (average n value of 1.14) (both available from Supresta), and bis-xylenylphosphate PX200(RXP) (available from Daihachi Chemical Industry Co. Ltd.). UV stability, hydrolytic stability and HDT (heat deflection temperature) values were obtained and compared and the results are illustrated in Examples 3-5 below. Each of the resin compositions also contained 0.30% by weight, of the total weight of the resin composition, PTFE (Teflon®) as an anti-dripping agent.

Example 3

UV Stability

PC/ABS composites containing, as flame retardants respectively, Fyrolflex RDP (n=1.28), Fyrolflex BDP (n=1.14), PX200 (RXP) (n value unavailable) and HDP (n=1.02) of the present invention (prepared in Example 1), were formulated in compositions of similar flammability (UL-94/V0, 1.6 mm flammability rated). The composites were extrusion compounded and further dispersed in the injection molding process. Of these moldings, test bars were prepared and placed in the Q-UV panel test for accelerated UV exposure. The four composites were equally exposed to UV irradiation in the testing device (Q-UV Panel tester) for about 500 hr. (UV light alone). The exposed samples were visually judged by five individuals for the degree of color degradation of each sample, giving a point value of one (best) for the composite with the least developed color and 5 (worst) to the compound with the highest color change and the results are reported in the table below.

| UV Stability Testing of FR-PC/ABS Composites* | | | | | | |
|---|---|---|---|---|---|---|
| PC/ABS (4/1) | Color Stability Ratings (1-Best to 5-worst) | | | | | Total |
| Neat PC/ABS | 1 | 1 | 1 | 1 | 1 | 5 |
| Fyrolflex RDP | 3 | 4 | 4 | 4 | 4 | 19 |
| Fyrolflex BDP | 2 | 3 | 2 | 3 | 3 | 13 |
| PX200 | 5 | 5 | 5 | 5 | 5 | 25 |
| HDP | 4 | 2 | 3 | 2 | 2 | 13 |

*+500 hr exposure - Q-UV Panel Tester

The UV stability of the PC/ABS composites described above were judged as follows (best to worst); neat PC/ABS; BDP and HDP; RDP; PX200 (RXP). In other words, the degree of color degradation of the PC/ABS composite containing the HDP of the present invention was surprisingly better than the degree of color degradation of the PC/ABS Fyrolflex RDP and PX200 and virtually the same as the PC/ABS composite containing Fyrolflex BDP.

Example 4

Hydrolytic Stability

Polycarbonate is susceptible to hydrolysis when exposed to high heat and humidity especially under acidic conditions, therefore flame retardants with better hydrolytic stability have less effect on de-stabilizing the polymer composite. Phosphate esters are sensitive to high heat and moisture and can hydrolyze to acid species and affect the stability of these composites.

In terms of hydrolytic stability, the PC/ABS resin containing the HDP having an average n value of about 1.02, as prepared in Example 1, showed unexpected improvement relative to the other flame retarded PC/ABS resin composites tested. The composites tested were formulated in FR-PC/ABS to UL94/V0 flammability specifications. The composite pellets were each prepared with the same Fyrolflex RDP, Fyrolflex BDP and PX200 (RXP) identified above and the hydroquinone bis(diphenylphosphate) (HDP) prepared in Example 1 and placed in sealed tubes with deionized water separated by glass wool. The stability of the PC portion of the composites relative to the blended flame retardant was measured after exposure to an accelerated environment. The setup for each of the tested materials were placed in an oven preset to a temperature of 107° C. for various time intervals.

It was determined that the hydrolytic stability of the PC/ABS resin composite containing the HDP of the present invention was better than the resin composites containing Fyrolflex RDP and Fyrolflex BDP and similar to the resin composite containing PX200 (RXP) at 90 hours. In particular, the hydrolytic stability of the resin containing the HDP of the present invention was better than the resins containing Fyrolflex RDP and Fyrolflex BDP. The PX200 (RXP) containing composite was more stable than the HDP containing composite in the early stages of exposure but showed similar levels of stability after ninety hours of accelerated exposure. The values shown in the table below are the average molecular weights of the polycarbonate of the composites tested measured using gas phase chromatography (GPC).

| PC/ABS | FR Additive Levels % | PC Molecular Weight (avg) | | |
|---|---|---|---|---|
| | | 0 hrs. | 30 hrs. | 90 hrs. |
| Fyrolflex RDP | 9 | 55000 | 46000 | 24000 |
| Fyrolflex BDP | 12.3 | 54000 | 49000 | 42000 |
| PX200 (RXP) | 12.3 | 62000 | 55000 | 49200 |
| HDP | 9 | 54500 | 53400 | 48900 |

Example 5

Heat Distortion Temperature

One of the key properties for any engineered resin is its heat distortion temperature (HDT) value. In the operation of electronic devices heat is generated in the appliance sourced from either a standard household current or remotely from batteries. If a composite has too low a HDT value for a given application, the plastic part may soften and be rendered useless for the device. Thus, phosphate compositions possessing a higher HDT are preferred over phosphate composites with lower HDT values since it often is a critical parameter in choosing the appropriate material.

The standard for testing this parameter is ASTM-D-648. Tested under similar loads (264 psi), the HDT values were determined for resin compositions containing, as a flame retardants, Fyrolflex RDP (same as above), Fyrolflex BDP (same as above), PX200 (RXP) (same as above) and the hydroquinone bis(diphenylphosphate) prepared in Example 1. Each of the compositions was prepared with enough flame retardant to provide compositions having comparable FR performance levels. The results are reported in the table below.

| PC/ABS | Additive Levels % | Heat Deflection Temperature* °C. @264 psi |
|---|---|---|
| Fyrolflex RDP | 9 | 84.4 |
| Fyrolflex BDP | 12.3 | 84.6 |
| PX200 (RXP) | 12.3 | 93.9 |
| HDP | 9 | 91.9 |

*ASTM-D648

As can be seen from the data above, the PC/ABS resin composite containing the HDP of present invention was found to be significantly better than both the resorcinol bis-(diphenylphosphate)(RDP) and bisphenol A bis-phosphate (BDP) analogues. The resorcinol bis-xylenylphosphate (PX200) analog was slightly higher when tested using the same protocol (ASTM-D648).

The overall performance of the four resin composites tested in Examples 3-5 were rated and the results presented in the chart below. Each resin composite containing, as a flame retardant, respectively, Fyrolflex RDP, Fyrolflex BDP, PX200 (RXP) and the hydroquinone bis-(diphenylphosphate) prepared in Example 1, was rated using a point value of 1 to represent the resin composition having the best UV stability (Example 3), hydrolytic stability (Example 4) and HDT (Example 5) as measured in each Example. In this comparison, the higher the number, the poorer the resin composite performed as compared to the other resin composites in the same Example. The values were then added together to give a single performance number, with the lowest number indicating the resin composite with the best overall combined performance for UV stability, hydrolytic stability and HDT.

| ADDITIVE | UV STABILITY Example 3 | HYDROLYTIC STABILITY Example 4 | HDT Example 5 | OVERALL PERFORMANCE |
|---|---|---|---|---|
| Fyrolflex RDP | 2 | 3 | 3* | 8 |
| Fyrolflex BDP | 1* | 2 | 3* | 6 |
| PX200 (RXP) | 3 | 1* | 1 | 5 |
| HDP | 1* | 1* | 2 | 4 |

*identical or similar performance in given test protocol.

As can be seen from the above data, the resin composite containing the HDP of the present invention demonstrates the best overall performance of all the resin composites tested. In other words, the resin composite containing the HDP of the present invention has the best combined UV stability, hydrolytic stability and HDT physical properties of the samples tested.

Example 6

| Flammability Results of FR-Polycarbonate Composites | | |
|---|---|---|
| Composite FR-PC Composites | Additive Level | UL94 (AFT) |
| PC-MF11/AF-098-T | 5 | V-0 (1.7) |
| PC-MF23/AF-098-T | 5 | V1 (3.7) |
| PC MF23/AF-098T/TPP | 5.0/0.3% | V-0 (0) |

PC/MF11 = Lexan 141, GE Plastics
PC/MF23 —Calibre 200, Dow
AFT = Average Flame Time Some polycarbonate resins were more difficult to flame retard (as tested by the UL94 protocol) possibly due to polymer branching and/or relatively high melt flow viscosity. For these resins it was found that simple doping of a vapor phase FR additive such as triphenyl phosphate could resolve these flammability issues. Other vapor phase FR additives useful for this purpose include monophosphate esters such as, Isopropylphenyl diphenyl phosphate, t-butylated phenyl diphenyl phosphate, cresylic phosphates. Additional vapor phase FR additives include Brominated polycarbonate oligomers, Brominated polystyrene, Potassium diphenyl sulphone sulphonate (KSS), Phosphinate salts, Ammonium polyphosphates, Melamine cyanurate, Melamine pyrophosphate.

Physical Properties of FR-Polycarbonate Composites

| Composite | Additive Level % | Tensile Strength psi | Flexural Modulus psi | Flexural Strength psi | HDT 264 psi °C. | Izod Impact ft.-lb/in |
|---|---|---|---|---|---|---|
| FR-PC Composites | | | $10^5$ | $10^3$ | | |
| PC-MF11/AF-098-T | 5 | 8766 | 3.95 | 15.0 | 107.8 | 0.95 |
| PC-MF23/AF-098-T | 5 | 8923 | 3.62 | 14.0 | 109.5 | 0.79 |
| PC MF23/AF-098T/TPP | 5.0/0.3% | 9091 | 3.8 | 15.0 | 105.6 | 0.9 |

PC/MF11 = Lexan 141, GE Plastics
PC/MF23 - Calibre 200, Dow

As triphenyl phosphate has more "plasticizing efficiency", the net effect of this doping shows nominal influence to other physical properties such as heat distortion temperature (slightly lowered) and impact strength (slightly improved). Other tested property results were considered within experimental range.

While the preferred embodiment of the present invention has been illustrated and described in detail, various modifications of, for example, components, materials and parameters, will become apparent to those skilled in the art, and all such modifications and changes are intended to fall within the scope of the claims of the present invention.

What is claimed is:

1. An oligomeric phosphate or mixture of oligomeric phosphates having the general formula I:

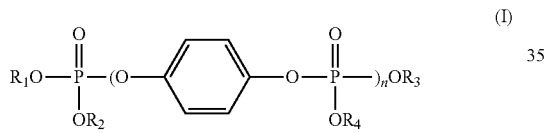

wherein $R_1$, $R_2$, $R_3$ and $R_4$ each independently is aryl or alkaryl and n has an average value of from about 1.0 to about 1.1 and wherein the oligomeric phosphate or mixture of oligomeric phosphates are in the form of a free-flowing powder having an average particle size of from about 10 μm to about 80 μm.

2. The oligomeric phosphate of claim 1 wherein $R_1$, $R_2$, $R_3$ and $R_4$ each independently is a phenyl group having the general formula II:

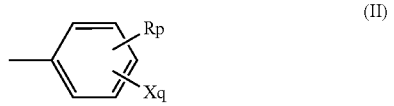

wherein each R independently is alkyl of 1 to 4 carbon atoms, each X independently is chlorine or bromine, p is 0 to 3 and q is 0 to 5 with the sum of p and q being 0 to 5.

3. The oligomeric phosphate a mixture of oligomeric phosphates according to claim 1 wherein $R_1$, $R_2$, $R_3$ and $R_4$ of formula I each is phenyl and n has an average value of 1.02.

4. A resin composition comprising;
(i) a flame retardant effective amount of an oligomeric phosphate or mixture of oligomeric phosphates having the following general formula I:

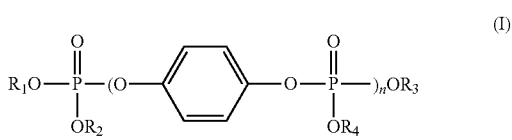

wherein $R_1$, $R_2$, $R_3$ and $R_4$ each independently is aryl or alkaryl and n has an average value of from about 1.0 to about 1.1 and wherein the oligomeric phosphate or mixture of oligomeric phosphates are in the form of a free-flowing powder having an average particle size of from about 10 μm to about 80 μm ; and
(ii) a resin.

5. The resin composition of claim 4 wherein $R_1$, $R_2$, $R_3$ and $R_4$ each independently is a phenyl group having the following general formua II,

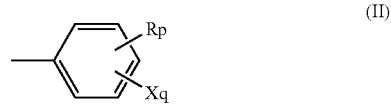

wherein each R independently is an alkyl of 1 to 4 carbon atoms, each X independently is chlorine or bromine, p is 0 to 3 and q is 0 to 5 with the sum of p and q being 0 to 5.

6. The resin composition of claim 4 wherein the resin is selected from a group consisting of styrenic polymers and copolymers, polyphenylene oxide (PPO), acrylonitrile butadiene styrene (ABS), polycarbonates (PC), high impact polystyrene (HIPS) and mixtures thereof.

7. The resin composition of claim 6 wherein the resin is PC/ABS or PPO/HIPS.

8. The resin composition of claim 4 wherein said resin composition contains from about 2% to about 20% by weight, of the total composition, of oligomeric phosphate or mixture of oligomeric phosphates flame retardants of formula I.

9. The resin composition of claim 4 wherein the oligomeric flame retardant of formula I is hydroquinone bis (diphenylphosphate).

10. The resin composition of claim 9 wherein said hydroquinone bis-(diphenylphosphate) has an average n value of about 1.02.

11. The resin composition of claim 5 wherein the resin is selected from a group consisting of styrenic polymers and copolymers, polyphenylene oxide (PPO), acrylonitrile butadiene styrene (ABS), polycarbonates (PC), high impact polystyrene (HIPS) and mixtures thereof.

12. The resin composition of claim 11 wherein the resin is PC/ABS or PPO/HIPS.

* * * * *